(12) United States Patent
Kim et al.

(10) Patent No.: US 8,880,514 B2
(45) Date of Patent: Nov. 4, 2014

(54) TERMINOLOGY-BASED SYSTEM FOR SUPPORTING DATA OBJECT DEFINITION

(75) Inventors: Hong Gee Kim, Seoul (KR); Seung Jae Song, Seoul (KR)

(73) Assignee: SNU R&DB Foundation, Seoul (KR)

( * ) Notice: Subject to any disclaimer, the term of this patent is extended or adjusted under 35 U.S.C. 154(b) by 82 days.

(21) Appl. No.: 13/643,705

(22) PCT Filed: Apr. 18, 2011

(86) PCT No.: PCT/KR2011/002749
§ 371 (c)(1),
(2), (4) Date: Nov. 5, 2012

(87) PCT Pub. No.: WO2011/136491
PCT Pub. Date: Nov. 3, 2011

(65) Prior Publication Data
US 2013/0046758 A1 Feb. 21, 2013

(30) Foreign Application Priority Data

Apr. 27, 2010 (KR) .................. 10-2010-0038824
Apr. 27, 2010 (KR) .................. 10-2010-0038825

(51) Int. Cl.
*G06F 17/00* (2006.01)
*G06F 17/30* (2006.01)
*G06F 19/00* (2011.01)

(52) U.S. Cl.
CPC ........ *G06F 17/30737* (2013.01); *G06F 19/324* (2013.01)
USPC .................................................. 707/723

(58) Field of Classification Search
None
See application file for complete search history.

(56) References Cited

U.S. PATENT DOCUMENTS

2007/0088559 A1* 4/2007 Kim .................................. 705/1
2010/0070302 A1* 3/2010 Murawski ......................... 705/3

FOREIGN PATENT DOCUMENTS

| KR | 10-2010-0033967 | 4/2011 |
| KR | 10-2010-0038824 | 10/2011 |
| KR | 10-2010-0038825 | 11/2011 |
| WO | WO 2011/136491 | 11/2011 |

OTHER PUBLICATIONS

Clinical Element Model, Joey Coyle, Yan Heras, Tom Oniki, Stan Huff, Nov. 14, 2008, 84 pages.*
SNOMED CT Basics, Aug. 2008, IHTSDO 2008 Used with permission.*

(Continued)

*Primary Examiner* — Robert Beausoliel, Jr.
*Assistant Examiner* — Hau H Hoang
(74) *Attorney, Agent, or Firm* — Ballard Spahr LLP

(57) ABSTRACT

The present invention relates to a terminology-system-based system for supporting data object definition, which delimits a concept by means of a qualifier. The terminology-system-based system for supporting data object definition stores a terminology system in which a concept is structured to a terminology object and a terminology relation, and stores a data object for the concept in order to define a data object for a selected concept (hereinafter, referred to as a corresponding concept). The terminology-system-based system for supporting data object definition comprises a qualifier recommendation unit, which receives a qualifier of the selected corresponding concept to define the corresponding concept, searches for a data object which is stored and defined as a concept which is the same as the corresponding concept (hereinafter, referred to as the same concept), and recommends a qualifier of the object. According to the above-described system, qualifiers of data objects to be newly defined are recommended by utilizing a constructed terminology system and construction information on predefined data objects. Therefore, new data objects can be more systematically and conveniently defined.

7 Claims, 6 Drawing Sheets

| DATA ENTITY (Data Element) | CONCEPT | QUALIFIER | VALUE SET |
|---|---|---|---|
| HOSPITAL A. ARTERIAL PRESSURE | ARTERIAL BLOOD PRESSURE | MEASUREMENT METHOD | COMPRESSION METHOD (INDIRECT METHOD), INVASIVE METHOD (DIRECT METHOD) |
| | | SYSTOLIC BLOOD PRESSURE | 0 ~ 999 mmHg |
| | | DIASTOLIC BLOOD PRESSURE | 0 ~ 999 mmHg |
| HOSPITAL B.ARTERIAL PRESSURE (1) | ARTERIAL BLOOD PRESSURE | MEASUREMENT METHOD | COMPRESSION METHOD (INDIRECT METHOD), INVASIVE METHOD (DIRECT METHOD) |
| | | MEASUREMENT POSTURE | STANDING, SITTING, LYING |
| | | MEASUREMENT SITE | LEFT UPPER ARM, RIGHT UPPER ARM, LEFT WRIST, RIGHT WRIST |
| | | SYSTOLIC BLOOD PRESSURE | 0 ~ 999 mmHg |
| | | DIASTOLIC BLOOD PRESSURE | 0 ~ 999 mmHg |
| HOSPITAL B.ARTERIAL PRESSURE (2) | ARTERIAL BLOOD PRESSURE | MEASUREMENT METHOD | COMPRESSION METHOD (INDIRECT METHOD), INVASIVE METHOD (DIRECT METHOD) |
| | | MEASUREMENT DEVICE | CATHETER |
| | | INSERTION SITE | RADIAL, BRACHIAL, AXILLARY, DORSALIS PEDIS, FEMORAL |
| | | SYSTOLIC BLOOD PRESSURE | 0 ~ 999 mmHg |
| | | DIASTOLIC BLOOD PRESSURE | 0 ~ 999 mmHg |
| | | MEAN ARTERIAL PRESSURE | 0 ~ 999 mmHg |

(56) References Cited

OTHER PUBLICATIONS

Binding Ontologies & Coding systems to Electronic Health, Records and Messages,Alan L Rector, School of Computer Science, University of Manchester, Journal of Applied Ontology vol. (1) pp. 51-69, (ISSN1570-5838 (Print) 1875-8533 (Online) DOI: 10.3233/AO-2009-0063 ).*

Combining mapping methods to align clinical archetypes to SNOMED CT, J.L. Allones, M. Taboada, M. Meizoso, D. Martinez, and S. Tellado, Engineering Conference (TKE 2012), pp. 326-328. Jun. 19-22, 2012, Madrid, Spain.*

Method and System for Classification of Clinical Information, WO 2011/075762 Al.*

A model-driven approach for representing clinical archetypes for Semantic Web environments, Catalina Martínez-Costa a, Marcos Menárguez-Tortosa a, Jesualdo Tomás Fernández-Breis a, José Alberto Maldonado, 2008 Elsevier Inc.*

Semantic Mapping of Clinicalmodel Data to Biomedical Terminologies to Facilitate Interoperability, Rahil Qamar, 2008.*

Automatic Mapping Clinical Notes to Medical Terminologies, Jon Patrick, Yefeng Wang and Peter Budd, Proceedings of the 2006 Australasian Language Technology Workshop (ALTW2006), pp. 75-82.*

SNOMEDClinical Terms® Abstract Logical Models and Representational Forms External Draft for Comment, Version 6b (Jan. 31, 2008).*

Post-Coordination in the Mapping of Interface Terms of a Clinical Wound Documentation System to SNOMED CT Martin Boekera, Stefan Schulza, ThiloSchuler, KR-MED 2008, May 31-Jun. 2, 2008, Phoenix, Arizona, USA.*

Comparing heterogeneous SNOMED CT coding of clinical research concepts by examining normalized expressions, James E. Andrews, Timothy B. Patrick, Rachel L. Richesson, Hana Brown, Jeffrey P. Krischer, doi:10.1016/j.jbi.2008.01.010.*

Ahn. "Detailed Clinical Model Development based on Standard Terminology for Structured Data." *Journal of 2008 KOSMI Fall Conference*. Nov. 22, 2008.

Boo, "Terminology Model Development for Integration of Health Care Terminologies." Presentation of 2006 2nd semester Seminars in Medical Informatics on Department of Health Policy and Management Seoul of National University College of Medicine. Sep. 27, 2006.

International Preliminary Report on Patentability issued by the International Bureau on Oct. 30, 2012 for PCT/KR2011/002749 filed on Apr. 18, 2011 and published as WO 2011/136491 on Nov. 3, 2011 (Applicant—SNU R&DB Foundation//Inventors—Kim et al.) (6 pages).

International Search Report and Written Opinion issued by the International Bureau on Dec. 28, 2011 for PCT/KR2011/002749 filed on Apr. 18, 2011 and published as WO 2011/136491on Nov. 3, 2011 (Applicant—SNU R&DB Foundation//Inventors—Kim et al.) (9 pages).

* cited by examiner

FIG. 6

| DATA ENTITY (Data Element) | CONCEPT | QUALIFIER | VALUE SET |
|---|---|---|---|
| HOSPITAL A. ARTERIAL PRESSURE | ARTERIAL BLOOD PRESSURE | MEASUREMENT METHOD | COMPRESSION METHOD (INDIRECT METHOD), INVASIVE METHOD (DIRECT METHOD) |
| | | SYSTOLIC BLOOD PRESSURE | 0 ~ 999 mmHg |
| | | DIASTOLIC BLOOD PRESSURE | 0 ~ 999 mmHg |
| HOSPITAL B.ARTERIAL PRESSURE (1) | ARTERIAL BLOOD PRESSURE | MEASUREMENT METHOD | COMPRESSION METHOD (INDIRECT METHOD), INVASIVE METHOD (DIRECT METHOD) |
| | | MEASUREMENT POSTURE | STANDING, SITTING, LYING |
| | | MEASUREMENT SITE | LEFT UPPER ARM, RIGHT UPPER ARM, LEFT WIRST, RIGHT WRIST |
| | | SYSTOLIC BLOOD PRESSURE | 0 ~ 999 mmHg |
| | | DIASTOLIC BLOOD PRESSURE | 0 ~ 999 mmHg |
| HOSPITAL B.ARTERIAL PRESSURE (2) | ARTERIAL BLOOD PRESSURE | MEASUREMENT METHOD | COMPRESSION METHOD (INDIRECT METHOD), INVASIVE METHOD (DIRECT METHOD) |
| | | MEASUREMENT DEVICE | CATHETER |
| | | INSERTION SITE | RADIAL, BRACHIAL, AXILLARY, DORSALIS PEDIS, FEMORAL |
| | | SYSTOLIC BLOOD PRESSURE | 0 ~ 999 mmHg |
| | | DIASTOLIC BLOOD PRESSURE | 0 ~ 999 mmHg |
| | | MEAN ARTERIAL PRESSURE | 0 ~ 999 mmHg |

TERMINOLOGY-BASED SYSTEM FOR SUPPORTING DATA OBJECT DEFINITION

CROSS REFERENCE TO RELATED APPLICATIONS

The present application is a National Phase Application of International Application No. PCT/KR2011/002749, filed Apr. 18, 2011, which claims priority to Korean Patent Application No. 10-2010-0038824, filed Apr. 27, 2010, and Korean Patent Application No. 10-2010-0038825, filed Apr. 27, 2010, which applications are incorporated herein fully by this reference.

TECHNICAL FIELD

The present invention relates to a terminology-based system for supporting data entity definition, which supports the definition of a data entity that specifies a term concept with a qualifier using a terminology system.

In particular, the present invention relates to a terminology-based system for supporting data entity definition, which searches for a data entity, which is defined as a concept that is the same as or related to a corresponding term concept, to extract a qualifier of the searched data entity and recommends the extracted qualifier as a qualifier of the corresponding term concept.

BACKGROUND ART

In general, a clinical document used in the medical field is a document of a patient's medical record and contains the patient's symptoms, a doctor's diagnosis and prescription, etc. Here, medical terms or medical data used in the clinical document to represent medical records are used differently by each medical worker or medical institution.

The medical terms or medical data require fast and accurate processing for their use and are required to ensure semantic and functional interoperability with other medical workers and support staff beyond one medical worker's use. In order to maintain these properties, it is necessary to construct a structural terminology system in the medical field so as to more easily obtain, collect, transfer, and process information contained in the clinical document.

With an existing data model-based terminology system, it is insufficient to achieve the above-mentioned object, and thus a supporting tool for structured data input is required. Furthermore, it can be said that the development of a terminology system for supporting the sharing of a clinical decision support system and an electronic health record is necessary.

First, it is necessary to clarify the concepts of medical terms used in the clinical document. This is because different terms are used for the same concept between medical workers, which makes it difficult to ensure smooth communication of information.

For this purpose, a terminology system which includes a set of medical concepts used in a specific medical field, the definition of each concept, the term for each concept, the relationship between concepts, etc. is being developed, and examples of the terminology system include a reference terminology, an interface terminology, etc. depending on its purpose and characteristics.

A reference terminology system is a set of standardized representations of medical concepts and their interrelationships and includes SNOMED CT, RxNorm, NCI Thesaurus, ICNP, etc.

Although there is the reference terminology system which is a set of standardized representations of medical concepts, local terms used by medical workers in various fields in each hospital are different, and thus a mapping operation is required to make up for the difference. In particular, it is necessary for the interface terminology to interface between the medical workers and the reference terminology system, and thus it is preferable that the interface terminology be configured based on the reference terminology system.

In order to solve the above-described problems, the present applicant discloses a terminology editing system based on a reference terminology, which constructs a terminology system in which the medical terms used in the medical institution are structured with entities and relations using a reference terminology system, in Korean Patent Application No. 10-2010-0033967, filed Apr. 13, 2010 (hereinafter, prior art 1).

When using the above prior art 1, it is possible to construct the interface terminology in the medical field to enable better communications between medical doctors or medical workers. However, the terminology system of the above prior art 1 can only support the structuralization of the concepts of terms in an accurate and systematic manner.

However, although the concepts of medical terms are structuralized, it is necessary to determine how the concepts are used in order to clearly understand the medical data for medical records). For example, if it is determined that the blood pressure is an arterial blood pressure and if it is whether the blood pressure is a systolic blood pressure or diastolic blood pressure, it is necessary to describe the condition in which the blood pressure is measured. Moreover in order to more clearly describe the patient's symptoms or the doctor's diagnosis, it is necessary to describe in more detail the severity, location, etc.

That is, the medical data should contain information on the context in which the data is created as well as the medical terms (or concepts). However, even in the same medical term, the context information may vary according to the medical worker or medical institution. A primary hospital may measure the blood pressure and describe only the values of the systolic and diastolic blood pressures. However, a tertiary hospital may further describe in detail a measurement means, a measurement site, a measurement posture, etc as well as the values of the systolic and diastolic blood pressures. This is because there may be subtle differences in the measurement results depending on the measurement conditions.

Therefore, it is necessary for the interface terminology system, which is designed such that a medical professional and a clinical support specialist can more easily obtain, collect, transfer, and process the information contained in the clinical document, to contain the context information to be processed and to have a supporting tool for structured data input such that the context information can be easily input in the medical field.

DISCLOSURE

Technical Problem

The prevent invention has been made in an effort to solve the above-described problems associated with the prior art, and an object of the present invention is to provide a terminology-based system for supporting data entity definition, which supports the definition of a data entity that specifies a concept with a qualifier using a terminology system.

Another object of the present invention is to provide a terminology-based system for supporting data entity definition, which searches for a concept that is the same as or related to a concept (hereinafter, referred to as a corresponding concept) of a data entity to be defined from a terminology system to extract a qualifier of the data entity that is already defined as the concept and recommends the extracted qualifier.

In particular, still another object of the present invention is to provide a terminology-based system for supporting data entity definition, which recommends a qualifier of a data entity, which is defined as a concept that is the same as or related to a corresponding term concept, based on a priority order, in which a rating weight of a definer that defines the data entity is reflected to preferentially recommend a qualifier that is used by the definer having the highest rating weight.

Yet another object of the present invention is to provide a terminology a ed. system for supporting data entity definition, which recommends a qualifier of a data entity, which is defined as a concept that is the same as or related to a corresponding term concept, based on a priority order, in which the priority order increases as the degree relationship with the corresponding concept decreases.

Technical Solution

In order to accomplish the above objects, the present invention provides a terminology-based system for supporting data entity definition, which supports the definition of a data entity that specifies a concept with a qualifier using a terminology system, the system comprising: a terminology system management unit which stores a terminology system in which the concept is structured with a term entity and a term relation; a data entity storage unit which stores the data entity with respect to the concept; a data entity definition unit which defines a data entity with respect to a selected concept (hereinafter, referred to as a corresponding concept) by receiving the selection of the corresponding concept and a qualifier that specifies the corresponding concept; and a qualifier recommendation unit which searches for a data entity, which is defined and stored as a concept (hereinafter referred to as the same concept) that is the same as the selected concept, and recommends a qualifier of the searched data entity.

In the terminology-based system for supporting data entity definition according to the present invention, the qualifier recommendation unit searches for a data entity, which is defined as a concept (hereinafter referred to as a related concept) that is related to the corresponding concept, and recommends a qualifier of the searched data entity, in which the related concept has a term relation with the corresponding concept.

In the terminology-based system for supporting data entity definition according to the present invention, the rating weight of the data entity is determined based on the rating of a definer that defines the data entity.

In the terminology-based system for supporting data entity definition according to the present invention, the qualifier recommendation unit recommends the qualifier of the data entity, which is defined as the same concept or the related concept, based on the priority order, in which the priority order increases as the degree of relationship with the corresponding concept decreases.

In the terminology-based system for supporting data entity definition according to the present invention, the qualifier recommendation unit preferentially recommends a qualifier that has the highest sum of the weights among the qualifiers having the same priority order based on the same degree of relationship, in which the sum of the weights of each qualifier (hereinafter referred to as a corresponding qualifier) is calculated as the sum of the rating weights of the data entity including the corresponding qualifier.

In the terminology-based system for supporting data entity definition according to the present invention, if the data entity (hereinafter referred to as a data concept of the same concept) which contains the corresponding qualifier and has the same concept is at least two, the sum of the weights of the corresponding qualifier is obtained, including the highest rating weight among the rating weights of the data entity of the same concept.

In the terminology-based system for supporting data entity definition according to the present invention, the qualifier recommendation unit recommends the qualifier by determining the priority order based on a relation weight assigned to the term relation.

In the terminology-based system for supporting data entity definition according to the present invention, the relation weight of the term relation is determined based on the type of the term relation.

In the terminology-based system for supporting data entity definition according to the present invention, the qualifier recommendation unit recommends the qualifier of the data entity, which is defined as the same concept or the related concept, based on the priority order, in which the priority order is proportional to the rating weight of the data entity containing the same concept or related concept and inversely proportional to the sum of the relation weights of the term relation.

In the terminology-based system for supporting data entity definition according to the present invention, the priority order is obtained as the sum $Q_i(C_M)$ of the weights by formula 1:

$$Q_i(C_M) = \sum_{R_k^M \in R(C_M)} \frac{1}{W(R_k^M)} \cdot q_i(C_k) \qquad \text{[Formula 1]}$$

wherein $q_i(C_k)$ is the sum of the rating weights of the qualifier in concept $C_k$, $W(R_k^M)$ is the sum of the relation weights of the term relation from concept $C_M$ to the same concept or related concept $C_k$, and $R(C_M)$ is a set of term relations between the corresponding concept $C_M$ and the same concept or related concept of the corresponding concept $C_M$.

In the terminology-based system for supporting data entity definition according to the present invention, the sum $q_i(C_k)$ of the rating weights of the qualifier in concept $C_k$ is obtained by the following formula 2:

$$q_i(C_k) = \sum_{D_j \in D(C_k)} W(D_j) \cdot q_i(D_j) \qquad \text{[Formula 2]}$$

wherein $q_i(C_k)$ is the sum of the weights of the qualifier in concept $C_k$, $q_i(D_j)$ is 1 if qualifier $q_1$ is in data concept $D_j$ and 0 if qualifier $q_1$ is not in data concept $D_j$, and $W(D_j)$ is the rating weight of data entity $D_j$.

In the terminology-based system for supporting data entity definition according to the present invention, the sum $q_i(C_k)$ of the rating weights of the qualifier in concept $C_k$ is obtained by the following formula 3:

$$q_i(C_k) = \text{Max}_{D_j \in D(C_k)} W(D_j) \cdot q_i(D_j) \qquad \text{[Formula 3]}$$

wherein $q_i(C_k)$ is the sum of the weights of the qualifier in concept $C_k$, $q_i(D_j)$ is 1 if qualifier $q_1$ is in data concept $D_j$ and 0 if qualifier $q_1$ is not in data concept $D_j$, and $W(D_j)$ is the rating weight of data entity $D_j$.

In the terminology-based system for supporting data entity definition according to the present invention, the qualifier recommendation unit does not recommend the qualifier if the degree of relationship with the corresponding concept exceeds a minimum recommendation degree of relationship.

Advantageous Effects

As described above, according to the terminology-based system for supporting data entity definition of the present invention, the medical terms used in the medical institution are constructed in a structured terminology system, and thus it is possible to structurally accumulate the patient's information, and thus it is possible to ensure the reusability of the information and the interoperability for the exchange of medical information.

Moreover, according to the terminology-based system for supporting data entity definition of the present invention, the qualifiers of data entities to be newly defined are recommended using structure information of predefined data entities, and thus it is possible to more conveniently define the new data entities.

Furthermore, according to the terminology-based system for supporting data entity definition of the present invention, when the qualifiers of the predetermined data entities are recommended by reference, the rating weight of the definer that defines the data entity is reflected such that the influence of the definer in the medical field is reflected, thus recommending more accurate qualifiers.

In addition, according to the terminology-based system for supporting data entity definition of the present invention, the priority order is assigned using the degree of relationship between the concepts, and thus it is possible to recommend the qualifier using the structure information accumulated in the terminology system and to more systematically define the new data entities.

DESCRIPTION OF DRAWINGS

FIG. 6 is a diagram showing an example of the definition of a concept and a qualifier of a data entity in accordance with an exemplary embodiment of the present invention.

Description of Reference Numerals

Figure 1A:
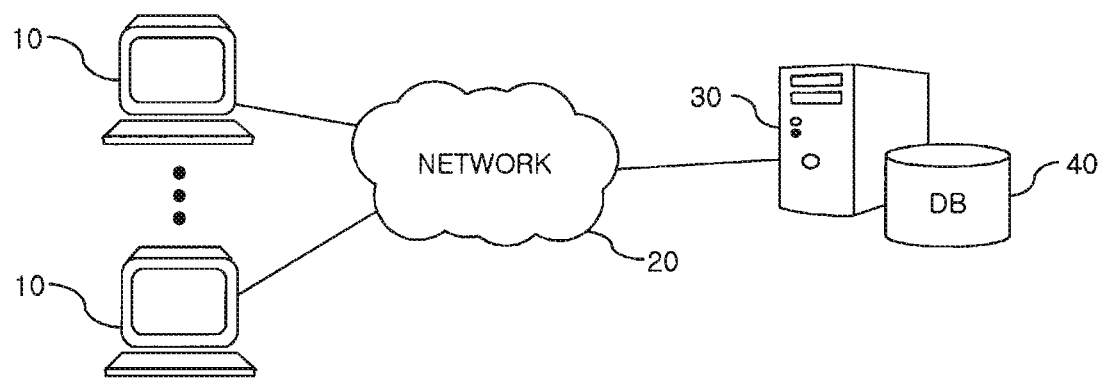
FIG. 1 is a diagram showing the configuration of the entire system for implementing the present invention.

10: user terminal  
20: network  
30: definition support system  
31: terminology system management unit  
32: data entity storage unit  
33: data entity definition unit -continued Description of Reference Numerals 34: qualifier recommendation unit  
40: database  41: terminology DB  
42: data entity DB

MODE FOR INVENTION

Hereinafter, exemplary embodiments for implementing the present invention will be described with reference to the accompanying drawings. In the following description, the same elements will be designated by the same reference numerals, and a repetitive description thereof will be omitted.

First, examples of the configuration of the entire system for implementing the present invention will be described with reference to FIG. 1.

Figure 1B:
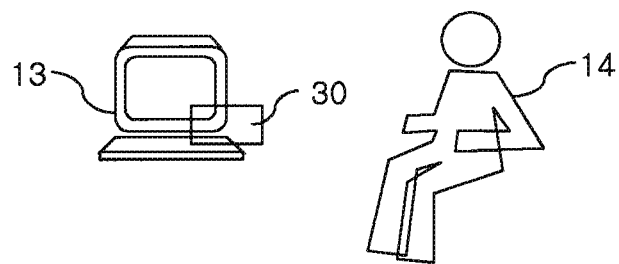

As shown in FIGS. 1a and 1b, a data entity definition support system according to the present invention may be implemented as a server system on a network or a program system on a computer terminal.

As shown in FIG. 1a, an example of the entire system for implementing the present invention comprises a user terminal 10 and a data entity definition support system 30 which are connected to each other through a network 20. The entire system may further comprise a data base 40 for storing necessary data.

The user terminal 10 is a typical computing terminal such as a PC, notebook, netbook, PDA, mobile, etc. used by a user such as a medical worker, a representative of a medical institution, etc. The user transmits medical terms or medical data used in his or her medical institution to the definition support system 30 using the user terminal 10 or requests the definition support system 30 to define the medical data.

The data entity definition support system 30 is a typical server and is connected to the network 20 to provide a service that provides a definition tool for the definition of the medical data, a service that displays the concepts of the medical terms for the definition of the medical data, or provide a service that displays qualifiers of predefined medical data to be referred to.

Meanwhile, the definition support system 30 may be implemented as a web server or web application server that provides each of the above services through a web page on the Internet.

The database 40 is a typical storage medium that stores data required by the definition support system 30 and stores terminology systems of medical terms, medical data entities created by the user, etc.

As shown in FIG. 1b, another example of the entire system for implementing the present invention comprises a data entity definition support system 30 in the form of a program that is installed in a computer terminal 13. That is, each function of the definition support system 30 is implemented as a computer program and installed in the computer terminal 13 to receive and register a concept (or term concept), a qualifier, etc. for the definition of a new data entity from the user through an input device or output a terminology system of medical terms, information on predefined data entities, etc. through an output device of the computer terminal 13. Meanwhile, the data required by the definition support system 30 are stored in a storage space such as a hard disk of the computer terminal 13 and used.

Next, the configuration of a terminology-based system for supporting data entity definition in accordance with an exemplary embodiment of the present invention will be described with reference to FIG. 2.

Figure 2:
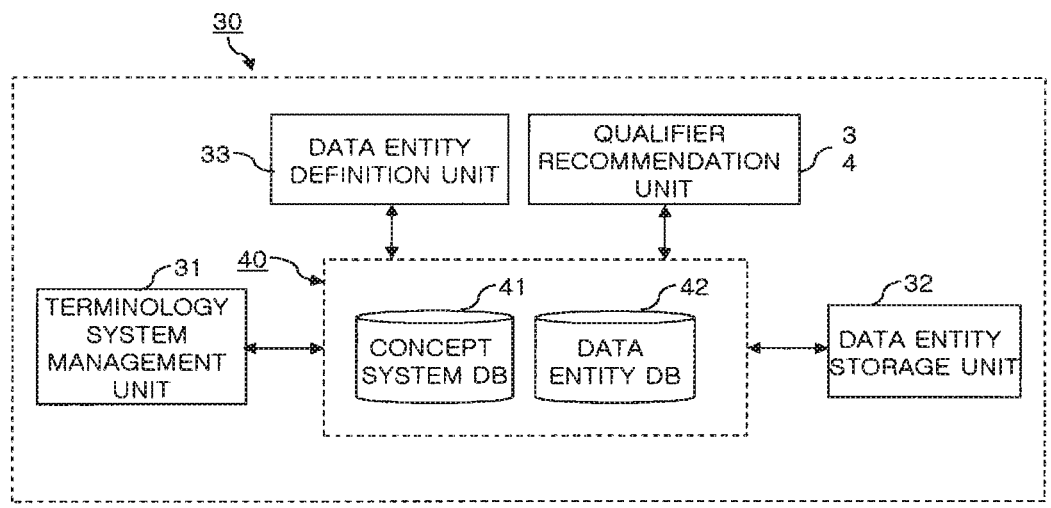
FIG. 2 is a block diagram showing the configuration of a terminology-based system for supporting data entity definition in accordance with an exemplary embodiment of the present invention.

As shown in FIG. 2, a terminology-based data entity definition support system 30 in accordance with an exemplary embodiment of the present invention comprises a terminology system management unit 31, a data entity storage unit 32, a data entity definition unit 33, and a qualifier recommendation unit 34. Additionally, the data entity definition support system 30 may further comprise a database (or storage space) 40 for storing data.

The terminology system management unit 31 stores a terminology system structured with entities and relations.

A terminology system in a narrow sense refers to a system of term concepts systemized by setting up each medical term as a concept, incorporating the same terms into the concept, and establishing the relation between the concepts. A terminology system in a broad sense refers to a system in which the medical terms used in the medical field are systemized and includes a system of medical data entities systemized by incorporating information on the context in which the medical terms are used as well as the systemized medical terms (medical concepts). In the following, the terminology system will be used as the terminology system in the narrow sense, and if it is necessary to distinguish between the terminology system in the narrow sense and the terminology system in the broad sense, the terminology system in the narrow sense will be described as a term concept system, and the terminology system in the broad sense will be described as a data entity or data entity system.

The terminology system (or term concept system) comprises a reference terminology system or a local terminology system (or interface terminology system) configured for each medical worker or medical institution. The reference terminology system is a set of standardized representations of medical concepts or medical terms and their interrelationships and includes SNOMED CT, RxNorm, NCI Thesaurus, ICNP, etc.

The terminology system is a storage space of relevant information on the concepts such as concept-based terms or relation information. The term may be a preferred term or a synonym or abbreviation for a pre-registered preferred term.

The terminology system may be represented as concepts and its association, and each may be structured with an entity and a relation. The entity and the concept, and the association and the relation are corresponding concepts, respectively, and thus will be used in a mixed manner. Moreover, the entity (or concept) comprises at least one of term properties, and any one of the term properties may be set as the preferred term. The preferred term may be used as the name of the entity.

Figure 3:
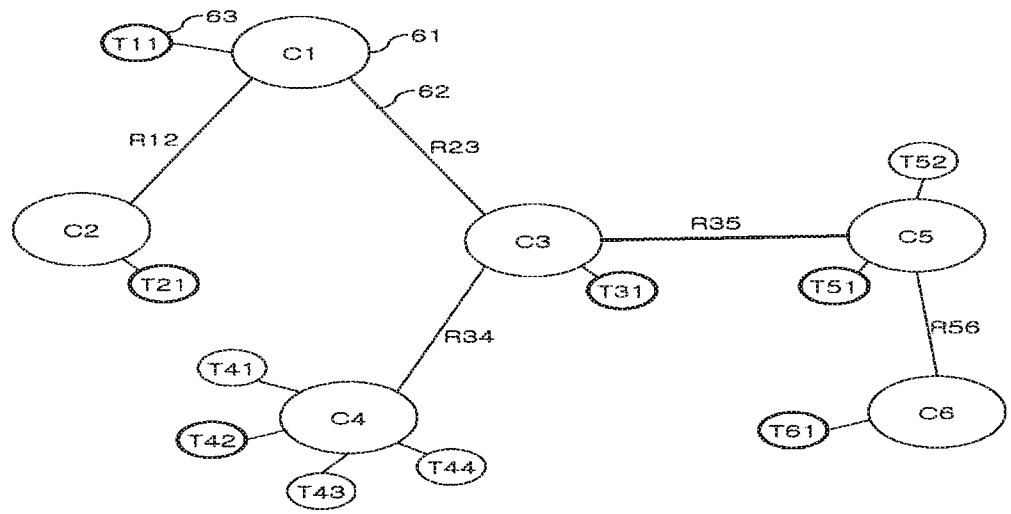
FIGS. 3 and 4 are diagrams showing the configuration and structure of a terminology system in accordance with an exemplary embodiment of the present invention.

Meanwhile, as shown in FIG. 3, the terminology system may be schematized as entity 61 and relation 62. In FIG. 3, entity 61 includes C1, C2, . . . , and C6, and the term includes T11, T21, . . . , and T61. Entity C4 has terms T41, T42, T43, and T44. Among them, term T42 is the preferred term.

Relation 62 is represented as R12, R23, . . . , and R56, each connecting the entities. Relation R12 is a relationship between entity C1 and entity C2, and relation R35 is a relationship between entity C3 and entity C5.

The relation is generally divided into a term relation and a mapping relation. The term relation includes a hierarchical relation that defines the relationship between a parent and a child with respect to two entities and a domain relation that defines an inclusive relationship of two entities. The mapping relation (or reference relation) refers to a relationship in which two entities are the same concept and correspond to each other. In FIG. 3, entities C1 and C2 have a hierarchical relation (or term relation). Entities C3 and C5 have a mapping relation. In the following, the mapping relation will also be described as the term relation. That is, the term relation in a broad sense will be used with a meaning that includes both the mapping relation and the term relation in a narrow sense.

Figure 4:
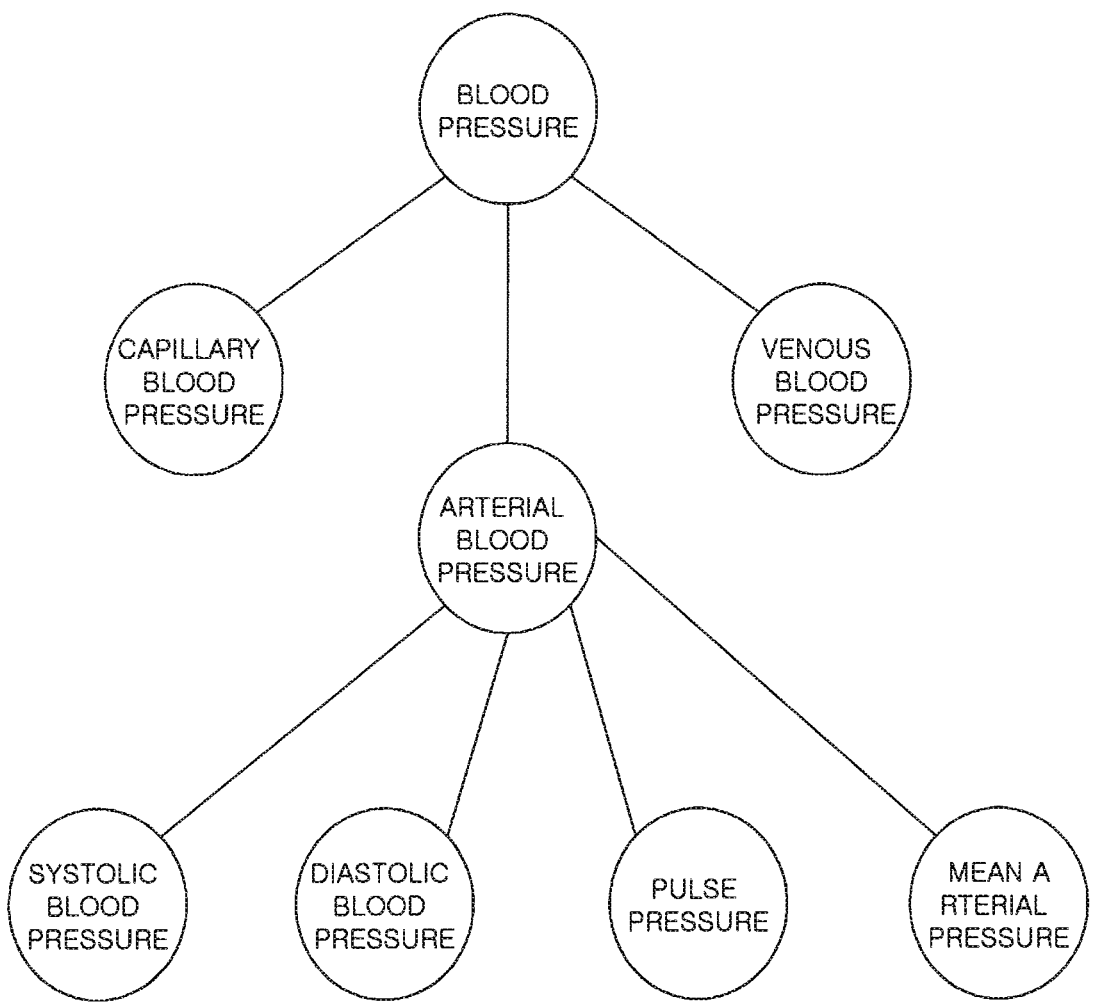

For example, the concept of blood pressure may be represented with an entity and a relation as shown in FIG. 4.

That is, the blood pressure is classified into arterial blood pressure, capillary blood pressure, and venous blood pressure according to the blood vessels, and the blood pressure typically refers to the arterial blood pressure. The arterial blood pressure varies according to heartbeats.

Moreover, the arterial blood pressure is classified into systolic blood pressure, diastolic blood pressure, pulse pressure, mean arterial pressure, etc. The systolic blood pressure refers to the maximum pressure in the blood vessel when blood in the ventricle is forced into the arteries by the myocardial contraction, and the diastolic blood pressure refers to the pressure in the vessels when the ventricles expand after the contraction of the heart.

Furthermore, the pulse pressure represents the difference between the systolic and diastolic blood pressures, and the mean arterial pressure refers to a mean value of the maximum arterial blood pressure and the minimum arterial blood pressure. In particular, the mean arterial pressure may be obtained from the systolic and diastolic blood pressures by a formula, but in a strict sense, it should be obtained by a computerized sphygmomanometer.

Next, the data entity storage unit 32 stores data entities with respect to the concepts.

Figure 5:
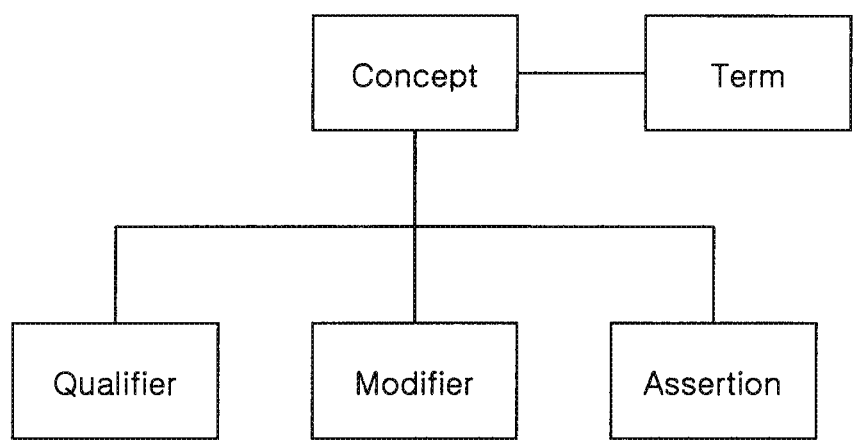
FIG. 5 is a diagram showing the configuration and structure of a data entity system in accordance with an exemplary embodiment of the present invention.

As shown in FIG. 5, a data entity comprises a concept, a term, a qualifier, a modifier, and an assertion. In addition, the data entity may further comprise a management element (not shown) for managing committed information, version information, history information, etc. to manage the terminology system.

Here, the qualifier, the modifier, and the assertion are elements that represent the context information.

The qualifier is generally used for the purpose of specifying the contents such as diagnosis, procedure, etc. That is, the qualifier may include a status post a procedure, a history of a specific condition, etc.

The modifier is generally used to describe in more detail the severity, location, etc. in describing the contents such as medical diagnosis. A value representing the severity includes mild, moderate, severe, etc. Moreover, the stages of the condition may be described as state I, stage II, etc.

The assertion (or assertional knowledge) is a concept proposed for the clarification of the meaning of the term concept. As the knowledge additionally provided to the definition of the term concept, information that is of help to the clarification of the concept such as relevant concepts, synonyms, common modifiers, etc. are provided by relevant clinical users. For example, chest pain does not appear in a healthy person, and the severity is represented as "mild", "moderate", and "severe". Moreover, the assertional knowledge may be represented as a difference between thorax pain and chest pain. Although both thorax pain and chest pain may be defined as the same concept through a conceptual "is-a" relationship, the thorax pain has a stronger meaning of pain location to a medical worker, and the chest pain may represent the possibility of cardiopulmonary disease.

The aforementioned qualifier, modifier, and assertion are all the context information that specifies the concept. In the following, all elements of the context information will be described as the qualifier As shown in FIG. 6, the data entity of the blood pressure may be configured with the concept (or term concept) and the qualifier.

In general, a doctor in a primary hospital (i.e., private hospital) measures the blood pressure by pressing an upper arm of a patient using a compression type sphygmomanometer and describes only the values of the systolic and diastolic blood pressures. Accordingly, the data entity with respect to the blood pressure measured by this hospital may be represented as "hospital A.arterial pressure" as shown in FIG. 6. That is, the data entity is represented as a measurement method, a value of systolic blood pressure, and a value of diastolic blood pressure.

However, during the measurement of the patient's blood pressure, there may be a slight difference in the measurement value depending on whether the measurement site is a right upper arm or left upper arm. Moreover, there is a difference in the measurement result depending on whether the patient is in a standing state, sitting state, or lying state.

Although such a minute difference is not important in the primary hospital, the minute difference may be very important in a tertiary hospital depending on the patient's condition. In this case, the data entity with respect to the blood pressure measured by this hospital may be represented as "hospital B.arterial pressure (1)" as shown in FIG. 6. That is, the data entity further comprises qualifiers such as a measurement posture and a measurement site, compared to the data entity of "hospital A.arterial pressure".

A value set is a set of values that the qualifiers can have. The value set of the measurement posture may have values such as standing (measured in a standing state), sitting (measured in a sitting state), and lying (measured in a lying state). Moreover, the measurement site may have values such as a left upper arm, a right upper arm, a left wrist, a right wrist, etc.

Meanwhile, in the tertiary hospital, the pressure in the arterial vessels may be directly measured instead of the above-described compression method. The direct measurement is widely used when it is difficult to measure the arterial blood pressure by the indirect measurement due to shock or hemorrhage, when it is necessary to continuously monitor the arterial blood pressure due to unstable cardiovascular status, or when it is necessary to frequently sample arterial blood so as to perform blood gas analysis or other blood tests. In this case, the mean arterial blood pressure may be measured to continuously monitor the blood pressure.

Accordingly, the data entity for this purpose may be presented as "hospital B.arterial pressure (2)" as shown in FIG. 6. That is, the data entity further comprises qualifiers such as a measurement device, an insertion site, and a mean arterial pressure, instead of the qualifiers of the measurement posture and the measurement site in the data entity of "hospital A.arterial pressure (1)". The insertion site is the location of the artery, into which a catheter is inserted, and may have values such as radial, brachial, axillary, dorsalis pedis, femoral, etc.

In the above example, the arterial blood pressure includes the systolic blood pressure and the diastolic blood pressure as its qualifiers. Thus, it can be seen that the qualifier itself is one of the concepts. That is, the measurement site, the mean arterial blood pressure, etc., which are used in the qualifier, may be defined as the concepts and may be the concepts included in the terminology system.

Next, the data entity definition unit 33 defines a data entity with respect to a selected concept (hereinafter, referred to as a corresponding concept) by receiving the selection of the corresponding concept and a qualifier that specifies the corresponding concept.

As previously discussed, the data entity comprises a concept and a qualifier. Preferably, the concept of the data entity is selected from the terminology system. That is, a medical worker selects the concept of the blood pressure that he or she wants from the terminology system so as to generate a data entity with respect to the blood pressure.

For example, the "arterial blood pressure" is selected from the terminology system as shown in FIG. 4. Typically, the blood pressure means the arterial blood pressure, and thus most doctors describe the arterial blood pressure as the "blood pressure" only in the clinical document. That the arterial blood pressure is described as "blood pressure 80-120", for example. Thus, it is possible to more accurately describe a medical term in the clinical document by selecting a corresponding concept from the terminology system.

The data entity definition unit 33 defines and generates a data entity by adding a qualifier and the like to the selected concept. Here, a qualifier appropriate for the selected concept is recommended by the qualifier recommendation unit 34.

That is, the qualifier recommendation unit 34 searches for a data entity, which is defined and stored as a concept (hereinafter referred to as the same concept) that is the same as the selected concept, and recommends a qualifier of the searched data entity. In particular, the recommendation unit 34 searches for a data entity, which is defined as a concept (hereinafter referred to as a related concept) that is related to the corresponding concept, and recommends a qualifier of the searched data entity, in which the related concept has a term relation with the corresponding concept.

The qualifier recommendation unit 34 recommends the qualifier of the data entity, which is defined as the same concept or the related concept, based on a priority order, in which the priority order increases as the degree of relationship with the corresponding concept decreases.

Moreover, the qualifier recommendation unit 34 preferentially recommends a qualifier that has the highest number of different concepts corresponding to the data entity whose qualifier is used among the qualifiers having the same priority order.

Moreover, the qualifier recommendation unit 34 recommends a qualifier of a data entity, which is defined as the same concept or the related concept, based on the priority order, in which the priority order is determined based on a rating weight assigned to each data entity.

The rating weight of the data entity is determined based on the rating of a definer that defines the data entity. The rating weight is assigned based on the influence of the definer in the medical field.

The data entity defined by the tertiary hospital has much more influence on the medical field than the data entity defined by the primary hospital. Moreover, even in the same primary hospital, a head hospital has a greater influence than a branch hospital. Furthermore, even in the same hospital, the influence is different depending on a medical worker (such as a doctor, nurse, medical officer, administrative officer, etc.) that defines the data entity. For example, the influence is different depending on a doctor, chief nurse, ordinary nurse, etc. Thus, different weights are determined by dividing the rating of each user or hospital based on the above-described influence.

In an exemplary embodiment, the rating weight is determined by various variables such as the number of beds, the rating of a hospital (primary, secondary, and tertiary), the title of a definer, the specialty, etc.

Preferably, if the rating weight of the definer is 3, all the rating weights of the data entities defined by the definer are determined as 3. In another exemplary embodiment, even if the same definer defines the data entity, it is preferable that the rating weight of the data entity be determined separately. For example, an administrator may determine the rating weight of a specific data entity to be specifically different.

Figure 7:
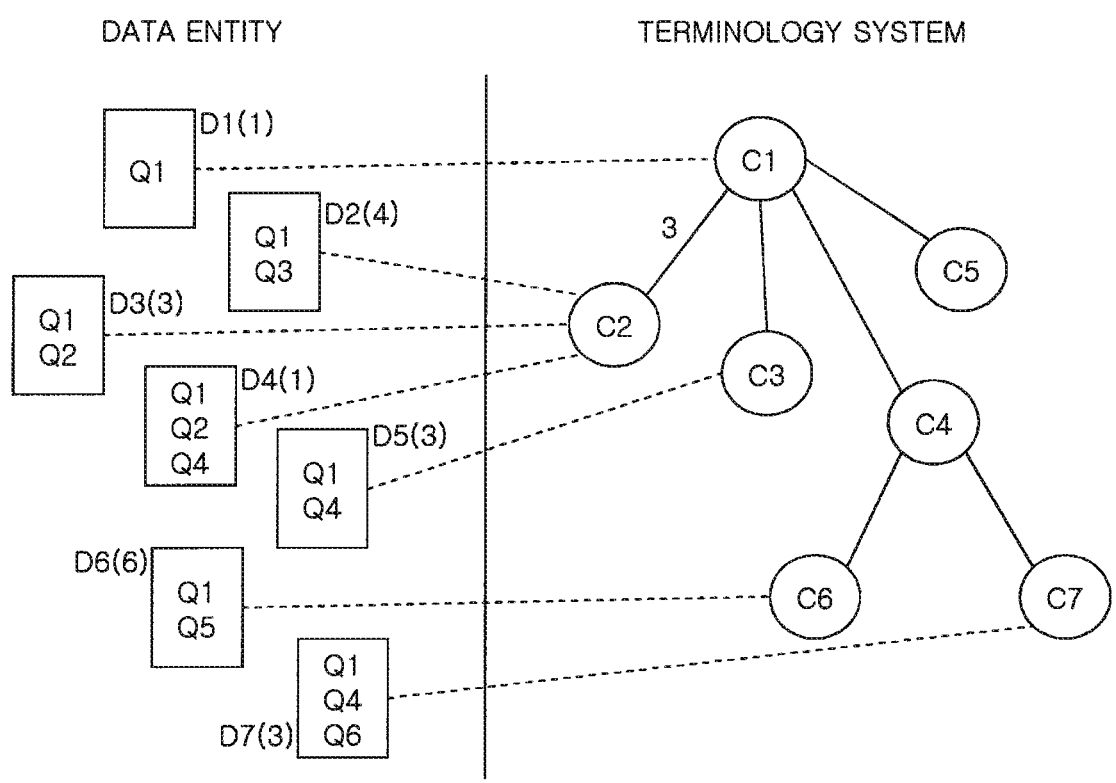
FIG. 7 is a diagram showing the relationship between a prebuilt terminology system and data entities which are previously generated and stored in accordance with an exemplary embodiment of the present invention.

An example in which the qualifier recommendation unit 34 recommends the qualifier in accordance with Example 1 of the present invention will be described with reference to FIG. 7 below. FIG. 7 is a diagram showing a prebuilt terminology system and data entities which are previously generated and stored.

The data entities are shown in the left side of FIG. 7, and the terminology system is shown in the right side of FIG. 7. D1, D2, . . . , and D7 denote the data entities, and Q1, Q2, . . . , and Q6 are the names of qualifiers. Moreover, C1, C2, . . . , C7 represent the concepts in the terminology system. The straight line connecting between the concepts in the terminology system represents the relation, and the dotted line connecting between the terminology system and the data entity represents the concept of a conceptual entity corresponding to the concept of the data entity.

Data entity D1 represents the definition of a data entity with respect to concept C1 and contains Q1 as its qualifiers. Moreover, data entity D2 represents the definition of a data entity with respect to concept C2 and contains Q1 and Q3 as its qualifiers. Furthermore, it can be seen there are three data entities D2, D3, and D4 with respect to concept C2. In addition, can be inferred that the concept of data entity D2 has a subordinate relation with the concept of data entity D1.

The recommendation of the qualifier under the conditions shown in FIG. 7 will be described for two cases below.

In the first case, the data entities corresponding to concept C2 are generated. The data entities defined as a concept that is the same as concept C2 are D2, D3, and D4. The qualifiers of these entities are Q1, Q2, Q3, and Q4. Thus, these qualifiers are recommended. Moreover, the related concept of concept C2 includes all of C1 to C7, and thus the data entities of the related concept are D1, D5, D6, and D7. The qualifiers of these entities are Q1, Q2, Q4, Q5, and Q6.

The qualifiers having the highest priority order are Q1, Q2, Q3, and Q4 of data entities D2, D3, and D4 which are defined as the same concept. Q1 and Q2 are used twice and Q3 and Q4 are used once as the qualifiers of the data entities, and thus qualifiers Q1 and Q2 have the highest priority order, and qualifiers Q3 and Q4 have the next priority order. Next, when qualifiers Q1 to Q4 are excluded from the qualifiers of the related concepts, qualifiers Q5 and Q6 remain, which all form a relation having a degree of relationship of 3. Thus, qualifiers Q5 and Q6 are recommended with the next priority order.

The degree of relationship represents the stages of the relationship between the concepts having a direct or indirect relationship in the terminology system. That is, the degree of relationship between C2 and C1 is 1, that between C2 and C3 to C5 is 2, and that between C2 and C6 and C7 is 3.

Meanwhile, if the degree of relationship with the corresponding concept exceeds a certain degree of relationship (i.e., a minimum recommendation degree of relationship), the recommendation may not be performed. For example, if the degree of relationship is limited to 8, the qualifier is not recommended any more when the degree of relationship exceeds 8.

Next, in the second case, the data entities corresponding to concept C5 are generated. There are no data entities that are defined and stored as the same concept as concept C5. The concept having a degree of relationship of 1 with concept C5 is C1, and the data entity of C1 is D1 only. Thus, qualifier Q1 of D1 is recommended with the highest priority order.

Then, qualifiers Q2, Q3, and Q4 of data entities D2 to D5 with respect to concepts C2 and C3 having the degree of relationship of 2 are recommended (Q1 is already recommended and excluded). Among them, Q2 is used three times, Q4 is used twice, and Q3 is used once.

However, when the qualifiers having the highest number of different concepts corresponding to the data entities whose qualifiers are used are calculated, Q4 is twice and both Q2 and Q3 are once. That is, Q2 is used in all data entities D2, D3, and D4 and thus is used three times, but is used only in concept C2. Thus, the number of different concepts used is 1. On the contrary, Q4 is used in data entities D4 and D5 and also used in concept C2 and C3, respectively. Thus, the number of different concepts used is 2.

Accordingly, the case where the number of times when the qualifiers are used is determined as the standard and the case where the number of different concepts of the used data entities is determined as the standard may have different results. In the latter case, the qualifiers used much more in the different concepts are much likely to be adopted. Thus, this is determined as the standard.

Lastly, when Q1 to Q4 are excluded from the qualifiers of the related concepts, Q5 and Q6 remain, which all form a relation having a degree of relationship of 3. Thus, qualifiers Q5 and Q6 are recommended with the next priority order.

Next, a method in which the qualifier recommendation unit 34 recommends the qualifier by determining the priority order based on the weight in accordance with Example 2 of the present invention will be described.

The qualifier recommendation unit 34 recommends a qualifier of a data entity, which is defined as the same concept or the related concept, based on the priority order, in which the priority order increases as the degree of relationship with the corresponding concept decreases. In particular, the qualifier recommendation unit 34 preferentially recommends a qualifier that has the highest sum of the weights among the qualifiers having the same priority order based on the same degree of relationship, in which the sum of the weights of each qualifier (hereinafter referred to as a corresponding qualifier) is calculated as the sum of the rating weights of the data entities including the corresponding qualifier.

That is the sum $q_i(C_k)$ of the rating weights of the qualifier in concept $C_k$ is obtained by the following formula 1:

$$q_i(C_k) = \sum_{D_j \in D(C_k)} W(D_j) \cdot q_i(D_j) \qquad \text{[Formula 1]}$$

In formula 1, $q_i(C_k)$ is the sum of the weights of the qualifier in concept $C_k$, $q_i(D_j)$ is 1 if qualifier $q_1$ is in data concept $D_j$ and 0 if qualifier $q_1$ is not in data concept $D_j$, and $W(D_j)$ is the rating weight of data entity $D_j$.

An example in which the qualifier recommendation unit 34 recommends the qualifier in accordance with Example 2 of the present invention will be described with reference to FIG. 7 below.

The recommendation of the qualifier under the conditions shown in FIG. 7 will be described for two cases below.

In the first case, the data entities corresponding to concept C2 are generated. The data entities defined as a concept that is the same as concept C2 are D2, D3, and D4. The qualifiers of these entities are Q1, Q2, Q3, and Q4. Thus, these qualifiers are recommended. Moreover, the related concept of concept C2 includes all of C1 to C7, and thus the data entities of the related concept are D1, D5, D6, and D7. The qualifiers of these entities are Q1, Q2, Q4, Q5, and Q6.

The qualifiers having the highest priority order are Q1, Q2, Q3, and Q4 of data entities D2, D3, and D4 which are defined as the same concept. The data entities containing Q1 are D2, D3, and D4, and thus the sum of the weights of Q1 is 4(D2)+3(D3)+1(D4)=8.

That is, when represented by formula 1, the sum $q_1(C_2)$ of the rating weights of qualifier Q1 in concept C2 is $q_1(C_2)$=4×1+3×1+1×1=8. Q2, Q3, and Q4 are all contained in the data entities, and thus their $q_i(C_k)$ is all 1.

In the same manner, the sum of the weights of qualifiers Q2, Q3, and Q4 is as follows.

$Q2:4×0(D2)+3×1(D3)+1×1(D4)=4$ (Q2 is not contained in D2, and thus the rating weight is 0)

$Q3:4×1(D2)+3×0(D3)+1×0(D4)=4$ $Q4:4×0(D2)+3×0(D3)+1×1(D4)=1$

Thus, Q1 has the highest priority order, Q2 and Q3 has the next highest priority order, and Q4 has the lowest priority order. Although qualifier Q3 appears once and Q2 appears twice, D2 has the highest rating weight, and thus Q2 and Q3 are recommended with the same priority order.

Then, when Q1 to Q4 are excluded from the qualifiers of the related concepts, Q5 and Q6 remain, which all, form a relation having a degree of relationship of 3. Thus, qualifiers Q5 and Q6 are recommended with the next priority order. However, since the sum of the rating weights of Q5 is 5 and the sum of the rating weights of Q6 is 1, Q5 is preferentially recommended.

The degree of relationship represents the stages of the relationship between the concepts having a direct or indirect relationship in the terminology system. That is, the degree of relationship between C2 and C1 is 1, that between C2 and C3 to C5 is 2, and that between C2 and C6 and C7 is 3.

Meanwhile, if the degree of relationship with the corresponding concept exceeds a certain degree of relationship (i.e., a minimum recommendation degree of relationship), the recommendation may not be performed. For example, if the degree of relationship is limited to 8, the qualifier is not recommended any more when the degree of relationship exceeds 8.

Next, in the second case, the data entities corresponding to concept C5 are generated. There are no data entities that are defined and stored as the same concept as concept C5. The concept having a degree of relationship of 1 with concept C5 is C1, and the data entity of C1 is D1 only. Thus, the sum of the weights of qualifier Q1 of D1 is 1, but Q1 is recommended with the highest priority order.

Then, qualifiers Q2, Q3, and Q4 of data entities D2 to D5 with respect to concepts C2 and C3 having the degree of relationship of 2 are recommended (Q1 is already recommended and excluded). The sum of the weights of qualifiers Q2, Q3, and Q4 is as follows.

$Q2:3(D3)+1(D4)=4$ $Q3:4(D2)=4$ $Q4:1(D4)+3(D5)=4$

Thus, the priority orders of Q2, Q3, and Q4 are all the same. Although qualifier Q4 appears twice in data entity D4 of concept C2 and data entity C5 of concept C3, qualifier Q4 has the same priority order as Q3 that appears once. This is because Q3 has the highest rating weight of the data entity.

Then, when Q1 to Q4 are excluded from the qualifiers of the related concepts, Q5 and Q6 remain, which all form a relation having a degree of relationship of 3. Thus, qualifiers Q5 and Q6 are recommended with the next priority order. However, since the sum of the rating weights of Q5 is 6 and the sum of the rating weights of Q6 is 3, Q5 is preferentially recommended.

Next, a method in which the qualifier recommendation unit 34 recommends the qualifier by determining the priority order based on the weight in accordance with Example 3 of the present invention will be described. Example 3 of the present invention is the same as Example 2 and has the following difference.

That is, if the data entity (hereinafter referred to as a data concept of the same concept) which contains the corresponding qualifier and has the same concept is at least two, the sum of the weights of the corresponding qualifier is obtained, including the highest rating weight among the rating weights of the data entity of the same concept.

That is, the sum $q_i(C_k)$ of the rating weights of the qualifier in concept $C_k$ is obtained by the following formula 2:

$$q_i(C_k)=\text{Max}_{D_j \in D(C_k)} W(D_j) \cdot q_i(D_j) \quad \text{[Formula 2]}$$

The first case of Example 2 will be described below. The sum of the weights of qualifiers Q2, Q3, and Q4 is as follows.

$Q1:\text{Max}\{4×1(D2),3×1(D3),1×1(D4)\}=4$ $Q2:\text{Max}\{4×0(D2),3×1(D3),1×1(D4)\}=3$ $Q3:\text{Max}\{4×1(D2),3×0(D3),1×0(D4)\}=4$ $Q4:\text{Max}\{4×0(D2),3×0(D3),1×1(D4)\}=1$ Thus, Q1 and Q2 have the highest priority order, Q3 has the next highest priority order, and Q4 has the lowest priority order. Although qualifier Q3 appears once and Q1 appears three times, Q1 and Q3 are all contained in D2 having the highest rating weight, and thus Q1 and Q3 are recommended with the same priority order. The rest is the same as Example 2.

The second case of Example 2 will be described below. That is, the second case is to generate data entities corresponding to concept C5, in which qualifier Q1 recommended, and then qualifiers Q2, Q3, and Q4 of data entities D2 to D5 with respect to concepts C2 and C3 having the degree of relationship of 2 are recommended (Q1 is already recommended and excluded). The sum of the weights of qualifiers Q2, Q3, and Q4 is as follows.

$Q2:\text{Max}\{3(D3),1(D4)\}=3$ $Q3:\text{Max}\{4(D2)\}=4$ $Q4:\text{Max}\{1(D4)\}+\text{Max}\{3(D5)\}=4$ Thus, Q3 and Q4 have the highest priority order, and Q3 has the next highest priority order. Although the rating weight of D2 in which Q3 is contained is higher than that of D5, Q4 contained in D5 is also contained in data entities D4 and D5 corresponding to concept C2 and C3, respectively, and thus their priority orders are the same. The rest is the same as Example 2

Next, a method in which the qualifier recommendation unit 34 recommends the qualifier by determining the priority order based on both the rating weight and the relation weight in accordance with Example 4 of the present invention will be described.

The qualifier recommendation unit 34 recommends the qualifier by determining the priority order based on the relation weight assigned to the term relation in addition to the rating weight assigned to the data entity. Preferably, the relation weight of the term relation is determined based on the type of the term relation.

As previously discussed, when the mapping relation is also considered as the term relation, the mapping relation is substantially the same relation, and thus it can be said that the related concept having the mapping relation the corresponding concept is the same as the same concept. Thus, it is preferable that the qualifiers of the data entities based on the related concept of the mapping relation be recommended with the same priority order.

For example, when the qualifiers of the data entity with respect to concept C1 are recommended in FIG. 3, the degree of relationship of concept C4 or C5 with concept C1 is 2. However, concepts C3 and C5 are in the mapping relation, and thus C1 and C5 are all in the degree of relationship of 1.

As such, the priority order to be recommended should be different based on the type of the term relation between the concepts. This is assigned as the relation weight. Preferably, the higher the relation weight, the lower the priority order. For example, if it is assumed that the relation weight of a parent relationship or inclusive relationship is 1, the relation weight of the mapping relation should be close to 0 or 0.1, and the term relation of the inverse relation should have a value much larger than 1, for example, a weight of 10.

Moreover, the administrator may determine the relation weight to be different even though the relation is of the same type such as the parent relationship. For example, in FIG. 3, the relation weight of R12 may be determined as 1.2, that of R23 may be determined as 0.8, and that of R35 may be determined as 0.3.

The qualifier recommendation unit 34 recommends the qualifier of the data entity, which is defined as the same concept or the related concept, based on the priority order, in which the priority order is proportional to the rating weight of the data entity containing the same concept or related concept and inversely proportional to the sum of: the relation weights of the term relation.

The priority of qualifier Q1 in concept $C_M$ is obtained as the sum $Q_i(C_M)$ of the weights by formula 3. That is, when the data entities corresponding to concept $C_M$ are generated, the sum of the weights of qualifiers Q1 to Q6 to be recommended is obtained by formula 3, and a qualifier having the highest weight is first recommended.

$$Q_i(C_M) = \sum_{R_k^M \in R(C_M)} \frac{1}{W(R_k^M)} \cdot q_i(C_k) \quad \text{[Formula 3]}$$

In formula 3, $q_i(C_k)$ is the sum of the rating weights of the qualifier in concept $C_k$, and $W(R_k^M)$ is the sum of the relation weights of the term relation from concept $C_M$ to the same concept or related concept $C_k$. Moreover, $R(C_M)$ is a set of term relations between the corresponding concept $C_M$ and the same concept or related concept of the corresponding concept $C_M$.

In formula 3, $q_i(C_k)$ is the sum of the weights of the qualifier in concept $C_k$, $q_i(D_j)$ is 1 if qualifier $q_1$ is in data concept $D_j$ and 0 if qualifier $q_1$ is not in data concept $D_j$, and $W(D_j)$ is the rating weight of data entity $D_j$.

Meanwhile, the sum $q_i(C_k)$ of the rating weights of the qualifier in concept $C_k$ is obtained by the above formula 1 or formula 2.

In Example 2 or 3, if the data entity (i.e., the data concept of the same concept) which contains the corresponding qualifier and has the same concept is at least two, Formula 2 is to obtain the sum of the weights of the corresponding qualifier, including the highest rating weight among the rating weights of the data entity of the same concept. Formula 1 is to add up the weights of the qualifiers which appear regardless of the data entity of the same concept.

For example, in FIG. 7, it is assumed that the relation weight between concepts C1 and C2 is 3 and the rest relation weights are all 1. Moreover, it is assumed that the qualifier is recommended to generate data entities corresponding to concept C5.

First, the recommendation of the qualifier based on formula 1 and formula 3 will be described.

The sum of the weights of Q1 is obtained as follows.

In the formulas, $C_M$ is C5, and $R(C_M)$ is a set of $R^5_1$(C5-C1), $R^5_2$(C5-C1-C2), $R^5_3$(C5-C1-C3), $R^5_6$(C5-C1-C4-C6), and $R^5_7$(C5-C1-C4-C7). This is because Q1 is contained in concepts C1 to C7, except for concept C4.

In the case of relation $R^5_1$(C5-C1), the relation is C5-C1 only, and thus the sum $W(R^5_1)$ of the relation weights is 1, the relation weight of C5-C1. Moreover, the sum $q_1(C_1)$ of the rating weights of Q1 in concept C1 is 1. Thus, the entire weight of Q1 in concept C1 is 1/1=1.

In the case of relation $R^5_2$(C5-C1-C2), the relation is C5-C1 and C1-C2, and thus the sum $W(R^5_2)$ of the relation weights is the sum of the relation weights of C5-C1 and C1-C2, 1+3=4. Moreover, the sum $q_1(C_2)$ of the rating weights of Q1 in concept C2 is 4(C2)+3(D3)+1(D4)=8. Thus, the entire weight of Q1 in concept C2 is 8/4=2.

By the above process, the entire weight of Q1 with respect to $R^5_3$(C5-C1-C3), $R^5_6$(C5-C1-C4-C6), and $R^5_7$(C5-C1-C4-7) is 3/2, 5/3, and 1/3, respectively. Moreover, the sum of the weights of Q1 is the sum of the entire weights of all relations, 1+2+3/2+5/3+1/3=7.5.

By the same process, Q2 to Q6 can be obtained as follows.

Q2:(3+1)/4=1

Q3:4/4=1

Q4:1/4+3/2=1.75

Q5:5/3=2;

Q6:3/3=1

Thus, the recommended priority order is Q1, Q5, and Q4, respectively, and Q2, Q3, and Q6 have the same priority order. That is, while the data entity of Q5 has the closest degree of relationship, it has the highest rating weight, and thus Q5 is recommended with the second priority order. According to Examples 2 and 3, the priority order is first determined based on the degree of relationship. However, in Example 4, the priority order recommended based on both the rating weight and the relation weight reflecting the degree of relationship is obtained.

Next, the sum of the weights obtained by formula 2 is as follows:

Q1:1/1+Max(4,3,1)/4+3/2+5/3+1/3=6.5

Q2:Max(3,1)/4=0.75

Q3:4/4=1

Q4:1/4+3/2=1.75

Q5:5/3=2

Q6:3/3=1

Compared to the previous cases, the priority order of Q2 is the lowest.

As described above, the invention made by the present inventor has been explained in accordance with the examples. However, the present invention is not limited to the examples, and various modifications can be made without departing from the scope of the invention.

INDUSTRIAL APPLICABILITY

The present invention is applicable to the development of a terminology-based system for supporting data entity definition, which supports the definition of a data entity that specifies a concept with a qualifier using a terminology system.

In particular, the present invention is applicable to the development of a terminology-based system for supporting data entity definition, which searches for a data entity, which is defined as a concept that is the same as or related to a corresponding term concept, to extract a qualifier of the searched data entity and recommends the extracted qualifier as a qualifier of the corresponding term concept.

The invention claimed is:

1. A terminology-based system, implemented on a server, for supporting data entity definition, which defines a data entity of a concept by setting at least one qualifier that specifies the concept, the terminology-based system comprising:
a terminology system management unit which stores a terminology system structured with a plurality of concepts and term relations which are relationships between the concepts;
a data entity storage unit which stores data entities of the concepts defined by setting at least one qualifier;
a data entity definition unit which, if a concept is selected from the terminology system, defines the data entity of the selected concept by setting qualifiers; and
a qualifier recommendation unit which searches for data entities of the same concept or a related concept to the selected concept, and recommends qualifiers of the searched data entities by a priority, wherein the related concept is connected to the selected concept within the terminology system by the term relations;
wherein a data entity definition unit sets some of the recommended qualifiers as qualifiers of the data entities of the selected concept; and
wherein the priority of a qualifier $q_i$, which belongs to the searched data entities, is obtained as a sum $Q_i(C_M)$ from formula 1:

$$Q_i(C_M) = \sum_{R_k^M \in R(C_M)} \frac{1}{W(R_k^M)} \cdot q_i(C_k) \quad \text{[Formula 1]}$$

where $C_M$ is the selected concept,
$C_k$ is the same concept as or the related concept to the concept $C_M$,
$q_i(C_k)$ is the sum of the rating weights of the data entities of the concept $C_k$ having a qualifier $q_i$,
$W(R_k^M)$ is the sum of the relation weights of the term relations from concept $C_M$ to the concept $C_k$,
$R_K^M$ is the term relations from the concept $C_M$ to the concept $C_k$, and
$R(C_M)$ is a set of term relations between the concept $C_M$ and the same concept as or the related concept to the concept $C_M$.

2. The terminology-based system of claim 1, wherein the term relation comprises a hierarchical relation that defines the relationship between a parent and a child with respect to two concepts and a domain relation that defines an inclusive relationship of two concepts.

3. The terminology-based system of claim 1, wherein the rating weight of the data entity is determined based on the rating of a definer that defines the data entity.

4. The terminology based system of claim 1, wherein the relation weight of the term relation is determined based on the type of the term relation.

5. The terminology-based system of claim 1, wherein the sum $q_i(C_k)$ of the rating weights is obtained by the following formula [2]:

$$q_i(C_k) = \sum_{D_j \in D(C_k)} W(D_j) \cdot q_i(D_j) \quad \text{[Formula 2]}$$

wherein $q_i(D_j)$ is 1 if qualifier $q_1$ is in data concept $D_j$ and 0 if the qualifier $q_1$ is not in data concept $D_j$, and $W(D_j)$ is the rating weight of data entity $D_j$,
$W(D_j)$ is the rating weight of data entity $D_j$, and
$D(C_k)$ is a set of data entities of the concept $C_k$.

6. The terminology-based system of claim 1, wherein the sum $q_i(C_k)$ of the rating weights is obtained by the following formula 3:

$$q_i(C_k) = \text{Max}_{D_j \in D(C_k)} W(D_j) \cdot q_i(D_j)$$

wherein $q_i(D_j)$ is 1 if qualifier $q_1$ is in data concept $D_j$ and 0 if qualifier $q_1$ is not in data concept $D_j$, and $W(D_j)$ is the rating weight of data entity $D_j$,
$W(D_j)$ is the rating weight of data entity $D_j$, and
$C(C_k)$ is a sum of data entities of the concept $C_k$.

7. The terminology-based system of claim 1, wherein the qualifier recommendation unit searches for data entities of only related concepts within a minimum recommendation degree of relationship with the selected concept.

* * * * *